United States Patent
Sherrod et al.

(10) Patent No.: US 7,264,615 B2
(45) Date of Patent: Sep. 4, 2007

(54) ABSORBENT INSERT FOR USE WITH AN OUTER ABSORBENT GARMENT

(75) Inventors: Earle Harry Sherrod, Appleton, WI (US); Stephen Bradford Cook, Appleton, WI (US); David Arthur Fell, Neenah, WI (US); Cornelis Jacobus Bosselaar, Appleton, WI (US); Courtney M. Nelson, Minneapolis, MN (US); Paul Joseph Datta, Appleton, WI (US); Mary Anne Bruemmer-Prestley, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 470 days.

(21) Appl. No.: 09/825,609

(22) Filed: Apr. 3, 2001

(65) Prior Publication Data

US 2002/0143316 A1    Oct. 3, 2002

(51) Int. Cl.
  *A61F 13/537* (2006.01)
  *A61F 13/72* (2006.01)
  *A61F 13/505* (2006.01)
  *A61F 13/535* (2006.01)

(52) U.S. Cl. ............ 604/385.14; 604/378; 604/385.03; 604/385.101; 604/364; 604/387

(58) Field of Classification Search ............... 604/364, 604/368, 378–385.01, 385.03, 385.101, 385.14, 604/387, FOR. 101, 393–396
See application file for complete search history.

(56) References Cited

U.S. PATENT DOCUMENTS

| | | | |
|---|---|---|---|
| 2,929,379 A * | 3/1960 | Poulsen ................. | 604/385.01 |
| 3,078,849 A * | 2/1963 | Morse | |
| 3,124,135 A * | 3/1964 | Olson ......................... | 601/368 |
| 3,563,242 A | 2/1971 | Hedstrom et al. | |
| 3,595,235 A | 7/1971 | Jespersen | |
| 3,612,054 A * | 10/1971 | Matsuda et al. ............ | 604/370 |
| 3,654,929 A * | 4/1972 | Nilsson et al. .............. | 601/368 |
| 3,658,062 A * | 4/1972 | Kapur ........................ | 604/368 |
| 3,658,064 A | 4/1972 | Pociluyko | |
| 3,667,468 A | 6/1972 | Nystrand et al. | |
| 3,769,978 A | 11/1973 | DeNight et al. | |
| 3,825,006 A | 7/1974 | Ralph | |

(Continued)

FOREIGN PATENT DOCUMENTS

EP    0 139 351    5/1985

(Continued)

OTHER PUBLICATIONS

Definition of "continuous", American Heritage Dictionary, 2nd ed., 2 pgs.*

(Continued)

*Primary Examiner*—Karin Reichle
(74) *Attorney, Agent, or Firm*—Brinks Hofer Gilson & Lione (57) ABSTRACT

An absorbent insert for use with an absorbent garment has a body-facing outer surface and a garment-facing outer surface. The garment-facing outer surface is at least partially permeable to fluids. The insert also includes one or more absorbent layers and one or more delay layer(s) adapted to substantially affect the flow of fluid through the insert.

15 Claims, 4 Drawing Sheets

U.S. PATENT DOCUMENTS

| | | |
|---|---|---|
| 3,886,941 A | 6/1975 | Duane et al. |
| 3,926,189 A | 12/1975 | Taylor |
| 4,019,517 A | 4/1977 | Glassman |
| 4,022,210 A | 5/1977 | Glassman |
| 4,036,234 A | 7/1977 | Ishizuka |
| 4,072,150 A | 2/1978 | Glassman |
| D259,211 S | 5/1981 | Larko |
| 4,265,245 A | 5/1981 | Glassman |
| D268,364 S | 3/1983 | Larko |
| 4,496,360 A | 1/1985 | Joffe et al. |
| 4,501,587 A | 2/1985 | Enloe |
| 4,573,986 A | 3/1986 | Minetola et al. |
| 4,573,989 A | 3/1986 | Karami et al. |
| 4,578,073 A | 3/1986 | Dysart et al. |
| 4,592,751 A * | 6/1986 | Gegelys ............... 604/368 |
| D284,891 S | 7/1986 | Larko et al. |
| 4,597,760 A | 7/1986 | Buell |
| 4,597,761 A | 7/1986 | Buell |
| D287,881 S | 1/1987 | Ternstrom |
| 4,643,726 A * | 2/1987 | Gegelys ............... 604/368 |
| 4,650,483 A | 3/1987 | Joffe |
| 4,657,538 A * | 4/1987 | Becker et al. ......... 604/381 |
| 4,676,786 A * | 6/1987 | Nishino |
| 4,795,455 A | 1/1989 | Luceri et al. |
| 4,806,408 A | 2/1989 | Pierre et al. |
| 4,834,737 A | 5/1989 | Khan |
| D302,854 S | 8/1989 | Minot |
| 4,892,598 A | 1/1990 | Stevens et al. |
| 4,938,756 A | 7/1990 | Salek |
| 4,963,139 A | 10/1990 | Dabroski |
| 4,964,857 A | 10/1990 | Osborn |
| 5,019,070 A | 5/1991 | Ruben |
| 5,043,206 A | 8/1991 | Ternstrom |
| 5,128,082 A | 7/1992 | Makoui |
| 5,160,331 A | 11/1992 | Forester et al. |
| 5,207,662 A | 5/1993 | James |
| 5,217,447 A | 6/1993 | Gagnon |
| 5,236,428 A | 8/1993 | Zajaczkowski |
| D340,977 S | 11/1993 | Provencher |
| D345,014 S | 3/1994 | Huffman |
| D348,102 S | 6/1994 | Gegelys et al. |
| D349,159 S | 7/1994 | Huffman |
| D350,196 S | 8/1994 | Huffman |
| D350,197 S | 8/1994 | Huffman |
| D350,198 S | 8/1994 | Huffman |
| 5,342,340 A | 8/1994 | Kichefski et al. |
| 5,360,422 A | 11/1994 | Brownlee et al. |
| D353,670 S | 12/1994 | Huffman |
| 5,378,528 A | 1/1995 | Makoui |
| 5,387,208 A | 2/1995 | Ashton et al. |
| 5,401,266 A | 3/1995 | Runeman et al. |
| 5,403,303 A | 4/1995 | Beplate |
| 5,405,342 A | 4/1995 | Roessler et al. |
| 5,409,476 A | 4/1995 | Coates |
| 5,423,787 A | 6/1995 | Kjellberg |
| 5,429,629 A | 7/1995 | Latimer et al. |
| 5,458,591 A | 10/1995 | Roessler et al. |
| 5,460,624 A | 10/1995 | Ahr et al. |
| 5,466,232 A | 11/1995 | Cadieux et al. |
| H1511 H | 12/1995 | Chappell et al. |
| 5,476,457 A | 12/1995 | Roessler et al. |
| 5,514,120 A | 5/1996 | Johnston et al. |
| 5,556,393 A | 9/1996 | Ronnberg |
| D378,407 S | 3/1997 | Bunton |
| 5,613,959 A | 3/1997 | Roessler et al. |
| 5,613,962 A * | 3/1997 | Kenmochi et al. |
| 5,643,240 A | 7/1997 | Jackson et al. |
| 5,647,862 A | 7/1997 | Osborn, III et al. |
| D384,150 S | 9/1997 | Gray et al. |
| D392,737 S | 3/1998 | Byer |
| 5,797,894 A | 8/1998 | Cadieux et al. |
| D398,055 S | 9/1998 | Burden |
| 5,817,081 A | 10/1998 | LaVon et al. |
| 5,846,230 A | 12/1998 | Osborn, III et al. |
| D411,007 S | 6/1999 | Peck |
| 5,910,137 A * | 6/1999 | Clark et al. ............ 604/387 |
| 5,925,026 A | 7/1999 | Arteman et al. |
| 5,938,650 A | 8/1999 | Baer et al. |
| 5,980,500 A | 11/1999 | Shimizu et al. |
| 5,994,615 A | 11/1999 | Dodge, II et al. |
| 6,060,638 A | 5/2000 | Paul et al. |

FOREIGN PATENT DOCUMENTS

| | | |
|---|---|---|
| EP | 0 319 314 | 6/1989 |
| EP | 0 549 988 | 7/1993 |
| EP | 0 627 178 | 12/1994 |
| EP | 0 667 136 | 8/1995 |
| EP | 0 763 353 | 3/1997 |
| EP | 0 945 110 | 3/1999 |
| EP | 1 005 847 | 6/2000 |
| WO | WO91 10413 A | 7/1991 |
| WO | 91/16871 | 11/1991 |
| WO | WO9506451 A1 * | 3/1995 |
| WO | 96/12459 | 5/1996 |
| WO | 96/29037 | 9/1996 |
| WO | 97/06765 | 2/1997 |
| WO | WO98 43574 | 10/1998 |
| WO | 00/37011 | 6/2000 |
| WO | 00/45762 | 8/2000 |

OTHER PUBLICATIONS

"Flush Safe" package label, at least as early as Mar. 1999.

* cited by examiner

ABSORBENT INSERT FOR USE WITH AN OUTER ABSORBENT GARMENT

FIELD OF THE INVENTION

The present invention relates generally to an absorbent insert for use with absorbent garments, such as adult incontinence garments, child diapers or training pants, and the like. More particularly, the present invention relates to an absorbent insert having one or more delay layers adapted to substantially affect the flow of fluid through the insert.

BACKGROUND

Absorbents garments are used extensively, by infants during toilet training, and by incontinent adults, to protect clothes from soiling. Absorbent garments are relatively effective in protecting the wearer's clothing as long as the amount of urine or other bodily waste contacting the garment does not exceed its absorbent capacity. However, a large insult of urine, or the occurrence of multiple insults between garment changings, can result in leakage of bodily exudates out of the sides of the garment, and into the wearer's clothing.

One attempt to avoid the leakage problem has been to add a removable, disposable insert into the outer absorbent garment. Such an insert supplements the absorbency of the outer absorbent garment. Furthermore, as a secondary advantage, an insert can gather relatively small insults of urine without soiling the outer absorbent garment. After the occurrence of a small insult, sometimes only the insert needs to be replaced, rather than the entire outer absorbent garment. Therefore, this strategy reduces not only the occurrence of leakage, but also the frequency of the need to clean or dispose of the outer absorbent garment, thereby reducing the cost to consumers.

A problem with the prior absorbent inserts is that they have typically been made with a fluid impermeable garment-facing surface. While the use of a fluid impermeable garment-facing surface prevents fluids from contacting the outer absorbent garment during small insults, it is counterproductive after a large insult of urine. Larger insults can force the urine to seep around the sides of the insert after the insert has been filled to its absorbent capacity, which can also lead to leakage from the outer absorbent garment. Because an infant or an incontinent adult typically has no control of whether he or she will experience a small or large insult of urine at a particular time, such inserts generally have not been successful. In contrast, an absorbent insert made with a fluid permeable garment-facing surface would typically allow fluid to contact the garment even during small insults, thereby eliminating the secondary advantage of using such an insert.

One particular prior absorbent insert, disclosed in European Patent Application 945,110, attempts to deal with this problem by providing an insert having an apertured garment-facing backsheet, which has its apertures covered by a liquid-impermeable covering sheet. The covering sheet is removably adhered to the outside of the backsheet, allowing the user to remove the covering sheet to allow the urine to pass through to an outer absorbent garment. The European Patent disclosure proposes that the insert may be worn without the impermeable covering sheet when the user is unable to frequently change the insert, such as during periods of sleep. In contrast, the insert may be used with the covering sheet when the user is able to frequently change the insert, such as during the day. However, because a user may experience a large insult even during the day, or may not know in advance whether he or she will have a convenient opportunity to change the insert, the strategy presented by the European Patent disclosure is largely ineffective.

Accordingly, there remains a need in the art for improved absorbent inserts for use with absorbent garments.

SUMMARY

In one aspect of the invention, an absorbent insert for use with an absorbent garment includes a body-facing outer surface and a garment-facing outer surface. The garment-facing outer surface is at least partially fluid permeable. The absorbent insert also includes at least one absorbent layer having a first primary surface and a second primary surface, and at least one delay layer adapted to substantially affect the flow of fluid passing through the insert. The delay layer(s) has a first primary surface and a second primary surface, and the surface area of each of the primary surfaces of the delay layer(s) is less than the surface area of each of the primary surfaces of the largest of the absorbent layer(s).

In another aspect of the invention, an absorbent insert for use with an absorbent garment includes a body-facing cover layer and a garment-facing cover layer. The garment-facing cover layer is at least partially fluid permeable. The absorbent insert also includes at least one absorbent layer having a first and second primary surface positioned between said body-facing cover layer and said garment-facing cover layer, and at least one delay layer having a first and second primary surface. The delay layer(s) is adapted to substantially affect the flow of fluid through the insert, and is positioned between the body-facing cover layer and the garment-facing cover layer.

In yet another aspect of the invention, an absorbent system includes an absorbent garment and an absorbent insert. The absorbent garment is adapted to be worn by a user, and has a body-facing surface and an outward-facing surface. The absorbent insert is adapted for use with the absorbent garment. The absorbent insert includes a body-facing outer surface and a garment-facing outer surface, at least one absorbent layer, and at least one delay layer. The garment-facing outer surface is at least partially fluid permeable. The absorbent layer(s) has a first primary surface and a second primary surface. The delay layer(s) is adapted to substantially affect the flow of fluid passing through the insert, and has a first primary surface and a second primary surface. The surface area of each of the primary surfaces of the delay layer(s) is less than the surface area of each of the primary surfaces of the largest of the absorbent layer(s).

Other aspects of the invention will be apparent to those skilled in the art in view of the claims that follow the detailed description.

DETAILED DESCRIPTION

Figure 1:
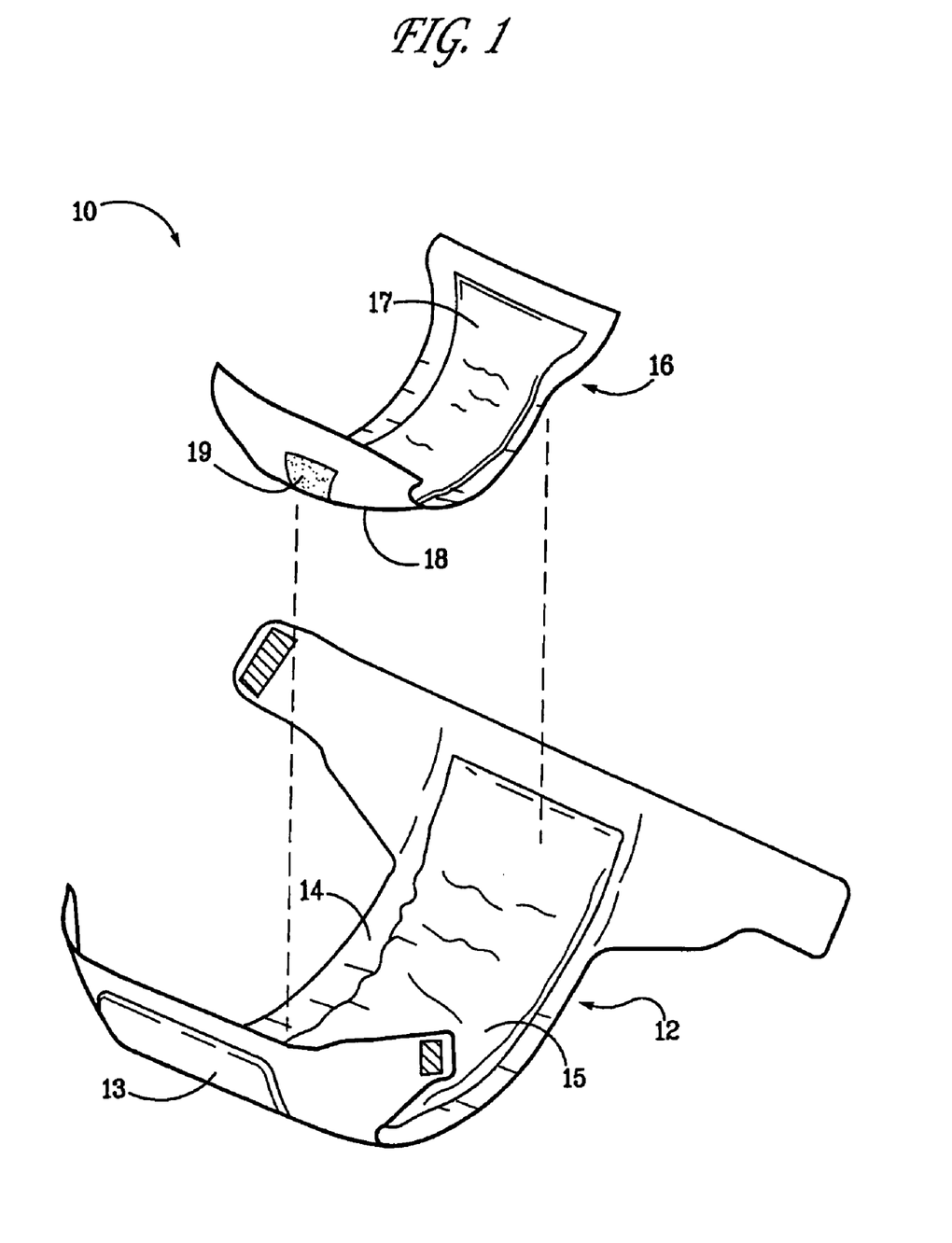
FIG. 1 is an exploded perspective view of an absorbent system in accordance with the present invention.

Referring now generally to the drawings and initially to FIG. 1, an absorbent system according to one embodiment of the present invention is shown as 10. The absorbent system 10 includes an outer, primary absorbent garment 12 and a supplemental absorbent insert 16. The absorbent garment 12 is adapted to be worn by a user around his or her waist. In the particular embodiment shown, absorbent garment 12 is a diaper of the sort used for an infant or a child not yet toilet trained, or for an incontinent adult. It should be readily appreciated by those of ordinary skill in the art that the present invention encompasses other such absorbent garments, such as training pants, incontinence pants, undergarments, briefs, or other garments adapted to be worn by a user and intended for absorbency of bodily exudates, such as urine or menses. The absorbent garment 12 may be made from disposable materials, or may be designed to be washed and reused.

The absorbent garment 12 includes an "outward-facing" surface 13 and a "body-facing" surface 14. The outward-facing surface 13 is made from a fluid-impermeable material in order to protect the user's clothes from being soiled. The "body-facing" surface 14 is designed to generally follow the contour of the user's body and to be placed generally adjacent to the body when worn by the user. The "body-facing" surface material is generally designed to be permeable to fluids, and preferably to wick away fluids from the body and trap them in one or more absorbent layers 15 within the garment. The various materials typically used for such garments, as well as the configurations of such garments, are well known in the art, and the present invention is not limited to any such specific materials or configurations of the absorbent garment.

The absorbent system 10 also includes a supplemental absorbent insert 16. The absorbent insert 16 is dimensioned and configured to be placed adjacent to the outer, primary absorbent garment 12 when the absorbent garment 12 is worn by the user. The absorbent insert 16 is designed to be removable from the absorbent garment 12, and to supplement the absorbency of the absorbent garment 12. The absorbent insert 16 includes a body-facing outer surface 17 and a garment-facing outer surface 18. The garment-facing outer surface 18 is intended to be positioned generally adjacent the body-facing surface 14 of the absorbent garment 12. While the absorbent insert 16 may just be simply positioned within the garment 12, the absorbent insert 16 preferably includes an attachment portion 19 for removably attaching or adhering the absorbent insert 16 to the absorbent garment 12. Typically, the attachment portion 19 will include an adhesive or one or more adhesive zones, however, those skilled in the art will appreciate that other attachment mechanisms, such as Velcro®, snaps, or buttons, for example, would also be suitable for removably attaching the absorbent insert 16 to the garment 12.

Figure 2:
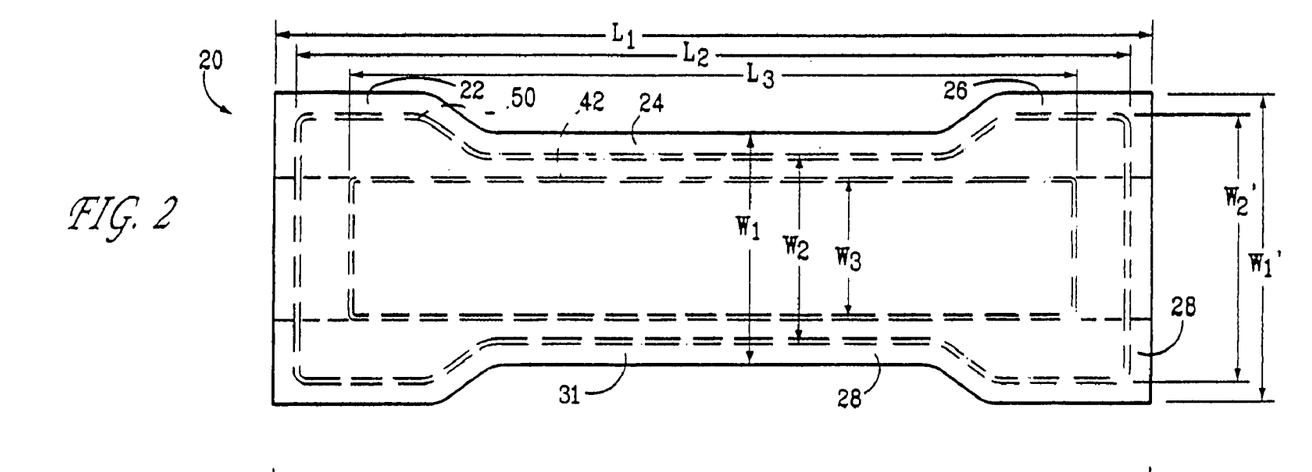
FIG. 2 is a top view of an absorbent insert according to one embodiment of the present invention.
Figure 3:
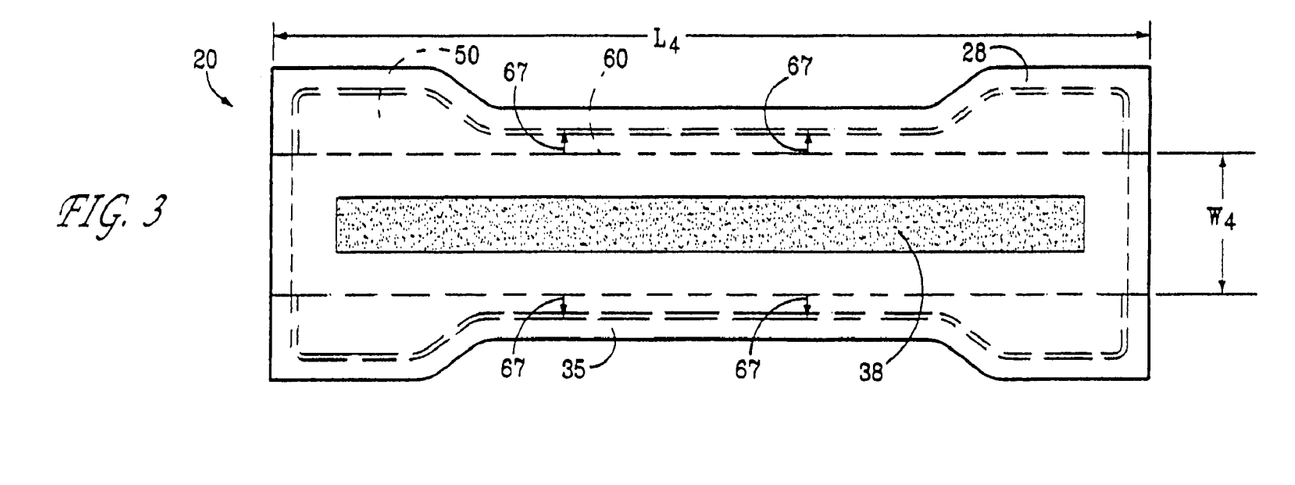
FIG. 3 is a bottom view of the absorbent insert of FIG. 2.
Figure 4:
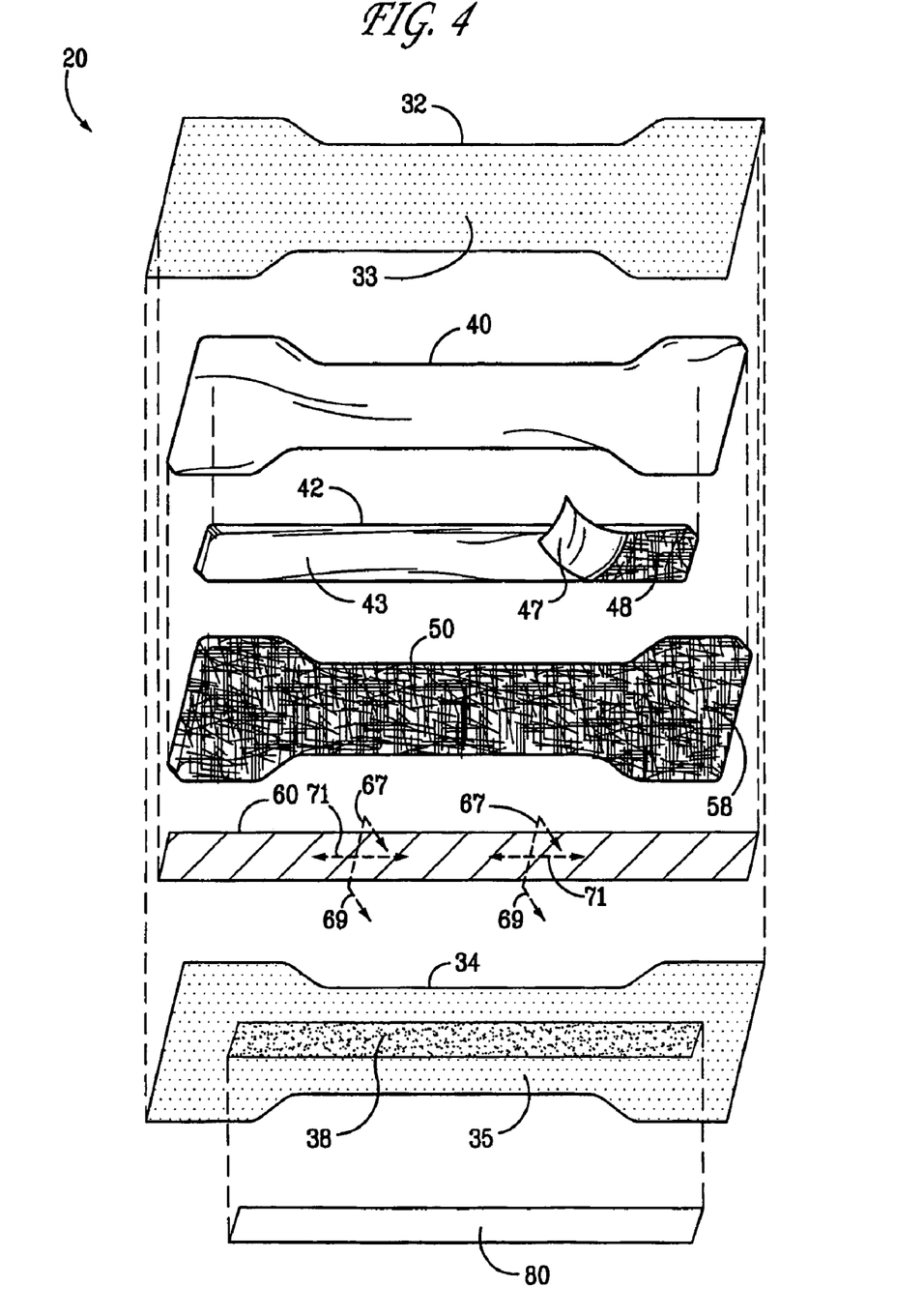
FIG. 4 is an exploded perspective view illustrating the garment-facing surfaces of the layers of the absorbent insert of FIGS. 2 and 3.

FIGS. 2-4 illustrate one preferred embodiment of an absorbent insert 20 that may be used in an absorbent system according to the present invention. FIG. 2 illustrates the top view of the body-facing outer surface 31 of the insert 20, while FIG. 3 illustrates the garment-facing outer surface 35 of the insert 20. When not in use, the insert 20 may be laid flat in a plane, as shown. Preferably, the insert 20 has an elongated and generally hour-glass shape or I-shape, which may dimensioned and configured for a particular absorbent garment. The insert 20 is elongated in a longitudinal direction defined by length L1, and has three integral portions along its length, including a central portion 24, connected at either side with end portions 22, 26, respectively. The insert 20 also has a lateral direction defined by one or more widths, $W_1$, $W_{1'}$, $W_2$, $W_{2'}$, $W_3$, and $W_4$. In the preferred embodiment, the central portion 24 has a width $W_1$, while the end portion 22, 26 have a width $W_{1'}$ which is larger than $W_1$. The widening of the end portions 22, 26 results in an insert having the hour-glass shape, which fits better to the contours of the body and may fit better with a particular absorbent garment. In alternate embodiments, the inserts of the present invention may have a consistent lateral width across the entire longitudinal direction. By way of example only, a typical adult incontinence insert will have an $L_1$ of about 20 cm to about 40 cm, a $W_1$ of about 7 cm to about 10.5 cm, and a $W_{1'}$ of about 7.5 cm to about 14 cm. The insert typically will have a total thickness of about 2 mm to about 40 mm, and more preferably about 8 to 15 mm. Those skilled in the art will appreciate that the insert is dimensioned and configured for the particular user and the particular outer absorbent garment, and therefore, for example, an insert for a child's diaper will have significantly smaller dimensions.

The insert 20 is a laminate, or multi-layer structure, as best seen with reference to FIG. 4, which illustrates an exploded perspective view of the garment-facing surfaces of all the layers. The insert 20 shown in FIGS. 2-4 includes a first cover layer 32, an intake or surge layer 40, a first absorbent layer 42, a second absorbent layer 50, a delay layer 60, a second cover layer 34, and an adhesive covering layer 80. The term "layer" as used herein is not limited to single unfolded sheets, but may include multiple or folded sheets or aggregations of fibers that generally constitute or function as a unit. The first cover layer 32 includes a body-facing surface (not shown in FIG. 4), which, in this embodiment, is the same as body-facing outer surface 31 (FIG. 2) of the insert 20. The cover layer 32 also includes an inward-facing surface 33, which faces the interior of the insert 20. The second cover layer 34 includes an inward facing surface (not shown) and a garment-facing surface, which, in this embodiment, is the garment-facing outer surface 35 of the insert 20.

The cover layers 32, 34 may be made from the same material, or from different materials. In one preferred embodiment, the cover layers 32, 34 are made from a single integral sheet which wraps and sandwiches the other layers, and then is cut to leave edges 28. Both the first cover layer 32 and the second cover layer 34 are at least partially permeable to liquids. Preferably, at least the first cover layer 32 is made from a material that will wick moisture away from the user's body. Suitable materials for the cover layers 32, 34 include a nonwoven web or sheet of wet strength tissue paper; a spunbonded, meltblown or bonded-carded web composed of synthetic polymer filaments, such as polypropylene, polyethylene, polyesters or the like; a web of natural polymer filaments such as rayon or cotton; apertured formed thermoplastic films and apertured plastic films; or biconstituent or bicomponent fibers, such as sheath/core polyethylene/polyethylene terephthalate fibers available from KoSa Fibers of Charlotte, N.C. The cover layers 32, 34 have a pore size that readily allows the passage therethrough of liquids, such as urine and other body exudates. The cover layers typically have a thickness of less than about 1 mm, and typically will have a basis weight of about 10 gsm to about 50 gsm, and more preferably, about 13-17 gsm. The cover layers 32, 34 may be selectively embossed or perforated with discrete slits or holes extending therethrough. Optionally, the web or sheet may be treated with a surfactant to aid in liquid transfer. One preferred cover layer material is a wettable spunbonded polypropylene having a basis weight of 17 gsm.

Furthermore, various formulations or additives, may be added to the body-facing outer surface 31, or to intake layer 40, or to the absorbent layers 42, 50, in order to enhance the comfort to the user. Examples of such formulations include lotions or emollients to soften and soothe the skin; irritation inhibiting agents, anti-inflammatory compounds, and powders, to ease the effects of chafing; anti-microbials, to help stop the spread of germs; and fragrances, extracts, and deodorants to help reduce odor. Those skilled in the art will recognize that any of the known formulations in the art may be selected for use with the absorbent insert.

Between the body-facing outer surface 31 and the garment-facing outer surface 35 of the second cover layer 34 are the intake layer 40, the absorbent layers 42, 50, and the delay layer 60. The intake or surge layer 40 is an optional layer that provides a temporary retention or absorption function for liquid not yet absorbed into the absorbent layers. The intake layer 40 tends to reduce fluid flowback or wetback from the absorbent layers to the cover layer 32. Suitable materials for the intake layer 40 include high bulk, compression resistant fibrous structures. It is preferred that the intake layer 40 be made from a fibrous material having a basis weight of at least 60 gsm, and be constructed and arranged to provide for an uptake time value of not more than 12 seconds, a liquid residual value of not more than about 1 gm of liquid per gram of the intake layer material, and a temporary loading value of at least about 3 gm of liquid per gram of the intake layer material. A particularly preferred intake layer material is an 85 gsm web made from about 40% denier PET fibers from BASF of Chandler, N.C., and about 60% denier PE/PET bicomponent fibers from KoSa Fibers of Charlotte, N.C. A typical intake layer 40 will have a thickness of about 1 mm to about 7 mm. Those skilled in the art, however, will recognize that any conventional intake or surge layer may be used in constructing the insert of the present invention.

The absorbent layers absorb and collect insults of urine or other bodily waste. In the preferred embodiment shown, there are two absorbent layers, however, in alternate embodiments, there may be only one absorbent layer, or multiple absorbent layers. The absorbent layers 42, 50 are preferably made from a highly absorbent material, shown as 48, 58, respectively. Preferably, the absorbent material of the first absorbent layer 42 is contained within a wrapping sheet 43. (The wrapping sheet 43 is shown with end portion 47 pulled back for illustrative purposes only). In the embodiment shown, only absorbent material 48 of absorbent layer 42 is wrapped, however, in an alternate embodiment, absorbent material 58 of absorbent layer 50 is also wrapped, or in other embodiments, none of the absorbent material in any of the layers are wrapped. The wrapping sheet 43 is preferably made from a high-wet-strength cellulosic tissue. Alternately, the wrapping sheet 43 may be a nonwoven material such as a rayon carded web that is bonded with poly(vinyl alcohol).

Suitable materials for the highly absorbent materials 48, 58 are well-known in the art. Preferred materials include air-formed wood pulp fluff, and/or highly-absorbency materials, including super-absorbent polymers (SAP) such as polyacrylic acid, sodium polyacrylate, polyacrylamide; other organic materials such as pectin, guar gum and peat moss; or inorganic materials including, for example, absorbent clays and silica gels. Preferably the absorbent materials include less than about 95 weight percent of wood pulp fluff and at least about 5 weight percent of high-absorbency materials. In a particularly preferred embodiment, absorbent material 48 is made from about 76% wood pulp fluff and 24% high-absorbency materials, and the absorbent material 58 is made from about 90% wood pulp fluff and about 10% high-absorbency materials. Where high-absorbency materials are incorporated, the materials may be distributed or otherwise incorporated into the layer in a substantially uniform or a nonuniform distribution. The absorbent material 58 may for example have a density from about 0.05 to about 0.3 grams per cubic centimeter and a basis weight from about 50 to about 700 gsm, and more preferably, about 496 gsm. One preferred type of wood pulp fluff, which is available under the trade designation CR1654 from U.S. Alliance Corporation of Coosa Pines, Ala., is a bleached, highly absorbent sulphate wood pulp containing softwood and hardwood fibers.

As shown in FIG. 2, the second absorbent layer has a length $L_2$ and widths $W_2$ and $W_2'$ that are smaller than, but are generally proportional to, and centered relative to, length $L_1$ and widths $W_1$ and $W_1'$, respectively, thereby leaving an border portion 28 where the first and second cover layer 32 and 34 may be bonded together. In the preferred embodiments, the difference between $L_1$ and $L_2$, the difference between $W_1$ and $W_2$, and the difference between $W_1'$ and $W_2'$ are typically about 10 mm to about 20 mm, and more preferably about 13.0 to 17.5 mm, thereby preferably leaving a border portion 28 having a dimension of about 6.5 mm to about 8.75 mm. Typically, the second absorbent layer will have a thickness of about 1 mm to about 40 mm.

Preferably, the first absorbent layer 42 has a length $L_3$ and a width $W_3$ that is smaller than and centered relative to length $L_2$ and width $W_2$. In especially preferred embodiments, the surface area of each primary surface of the first absorbent layer 42 is less than the surface area of each primary surface of the second absorbent layer 50. As used herein, a "primary surface" of a layer includes the largest first and second parallel surfaces of the layer that lie in the plane of the insert. Thus, a primary surface is distinct from the smaller edges of the layer, such as those defining the thickness of the layer. In a typical adult incontinence insert, $L_3$ is about 20 cm to about 26 cm. Those skilled in the art, however, will appreciate that the length of the first absorbent layer 42 will vary based upon the size of the overall insert 20, and upon the particular user and the particular outer absorbent garment for which the insert 20 is designed. Typically, the first absorbent layer 42 will have a thickness of about 2 mm to about 20 mm, and more preferably, about 6 mm to about 10 mm.

The delay layer 60 of the present invention functions to maximize the absorbent capacity of the absorbent insert 20. The delay layer operates to substantially affect the flow of fluid through the insert. As used herein, "substantially affect the flow" means that the delay layer substantially impacts or alters the aggregate flow of fluid to a degree that would not be expected in a flow profile of fluid through an insert made only with conventional absorbent materials and covering layers. This substantial affect may cause a substantial change to flow direction, leading to the flow of fluid to be substantially redirected. For example, the fluid may be distributed into areas of the absorbent layers that would not normally be reached by unimpeded flow of fluid. As used herein, "substantial change to flow direction" means that the aggregate flow of the fluid transversing the insert will change to an appreciable extent not accounted for by gravity, hydrostatic pressure, and/or wicking of the fluid through the materials making up the other layers of the insert. In especially preferred embodiments, the delay layers of the present invention substantially change the flow direction of a fluid that, before contacting the delay layer, is traveling generally in the direction from the body-facing outer surface to the garment-facing outer surface, in a direction generally normal to the plane defined by the longitudinal direction and the lateral direction of the insert. Alternately, or in addition to a substantial change in flow direction, the delay layer may partially inhibit the flow of fluid through the insert. As used herein, "to partially inhibit" means that while the delay layer will allow to some extent movement of the fluid through the insert, it will either slow the fluid, allow the fluid only to flow after a specific length of time, or only at a certain concentration.

The delay layers of the present invention may be made from a substantially fluid impermeable material, or from a material that is at least partially fluid permeable. A partially permeable material acts to partially inhibit the flow of fluid through the insert by causing the fluid to move at a much slower rate. Examples of suitable partially permeable materials include apertured plastic and thermoplastic films. A delay layer made from a partially permeable material should have a degree of fluid permeability less than that of the covering layers 32, 34.

When the delay layer is made from a fluid impermeable material, the delay layer substantially affects the movement of fluids by substantially changing the flow direction, such as redirecting or distributing the fluid into remote regions of the absorbent layers, and/or partially inhibiting the fluid as its flows through the insert. Suitable materials for a substantially impermeable delay layer include polypropylene, polyethylene, or nylon. Especially preferred materials for the delay layers are those that are at least partially water-soluble. A water-soluble delay layer can be used to temporarily delay penetration of small insults of bodily waste through the insert, dissolving only when in contact with a relatively large insult, or when the insert becomes saturated. An especially preferred partially water-soluble material is poly(vinyl alcohol) (PVOH). A delay layer made from poly(vinyl alcohol) can absorb up to 150 ml of urine before dissolving.

In the embodiment shown, the delay layer 60 is made from a fluid impermeable material. The delay layer 60 is positioned between the second cover layer 34 and the second absorbent layer 50, and thus, between the body-facing outer surface 31 and the garment-facing outer surface 35. As shown in FIG. 3, the delay layer 60 has a length $L_4$ and a width $W_4$. In the embodiment shown, $L_4$ is equal to $L_1$. However, $L_4$ may be the same, smaller, or larger than any of $L_1$, $L_2$, or $L_3$. Likewise, $W_4$ may be the same, smaller, or larger than any of $W_1$, $W_2$, or $W_3$. In a typical adult incontinence insert, by way of example only, $L_4$ is about 20 cm to about 32 cm, and $W_4$ is about 3.5 cm to about 5.5 cm. A typical delay layer thickness is about 0.01 mm to about 0.1 mm, and more preferably, about 0.025 mm.

Although $L_4$ and $W_4$ each may generally be selected independently relative to the other dimensions of the insert 20 and the absorbent layers 42, 50, the surface area of each of the primary surfaces of the delay layer, defined by $L_4 \times W_4$, is particularly relevant to its effectiveness. In preferred embodiments, each primary surface of the delay layer 60 has a surface area less than the surface area of each of the primary surfaces of the largest absorbent layer (here, the second absorbent layer 50). In especially preferred embodiments, the ratio of the area of each of the primary surfaces of the largest absorbent layer to the area of each of the primary surfaces of the delay layer is in the range of about 4:1 to about 1.01:1, more preferably about 2.2:1 to about 1.05:1, and most preferably about 1.5:1. When the delay layer 60 has a smaller primary surface area than the largest absorbent layer 50, the delay layer 60 is particularly effective in distributing and redirecting the urine to maximize the absorbent capacity of the absorbent layers, while still allowing for the passage of larger insults, as more fully described below. In the embodiment shown, each of the primary surfaces of the delay layer 60 have a surface area greater than each of the primary surfaces of the smaller first absorbent layer 42; however, in alternate embodiments, the surface area of the primary surfaces of the delay layer 60 may be equal to or smaller than the surface area of the primary surfaces of the first absorbent layer 42.

The delay layer 60 of insert 20 in the embodiment shown substantially affects the movement of fluid through the insert 20. The delay layer 60, which is flat and planar in the embodiment shown, accomplishes this by forcing fluid traveling generally normal to a central portion of the plane of the insert to substantially change its direction upon contact with the impermeable material. This forces the fluid to travel laterally, as indicated by line 67, and longitudinally, as indicated by arrows 71 (see FIG. 4), thereby forcing the fluid to more fully contact the full length and lateral extent of the second absorbent layer 50. As long as the maximum volume of fluid that can be held by the absorbent layer 50 is not reached, the fluid is not likely to continue down through the second cover layer 34 and thus will not soil or penetrate the garment-facing outer surface 35. The practical effect is that insert 20 will hold insults of urine or other fluids up to its full capacity, without allowing a narrow stream of urine from a small insult to soil the primary outer absorbent garment. However, at the same time, the delay layer 60 will allow volumes of urine that exceed the capacity of the absorbent layers to flow around the delay layer 60, as shown by arrow 69 in FIG. 4, and into the outer absorbent garment.

The insert 20 also includes an attachment portion, shown in FIG. 4 as an adhesive zone 38. A removable adhesive covering layer, such as a peel strip or film, covers the adhesive zone until the insert 20 is ready for use. The adhesive covering layer 80 is removed and the insert 20 is firmly pressed into the absorbent garment so that it will be properly positioned.

Figure 5:
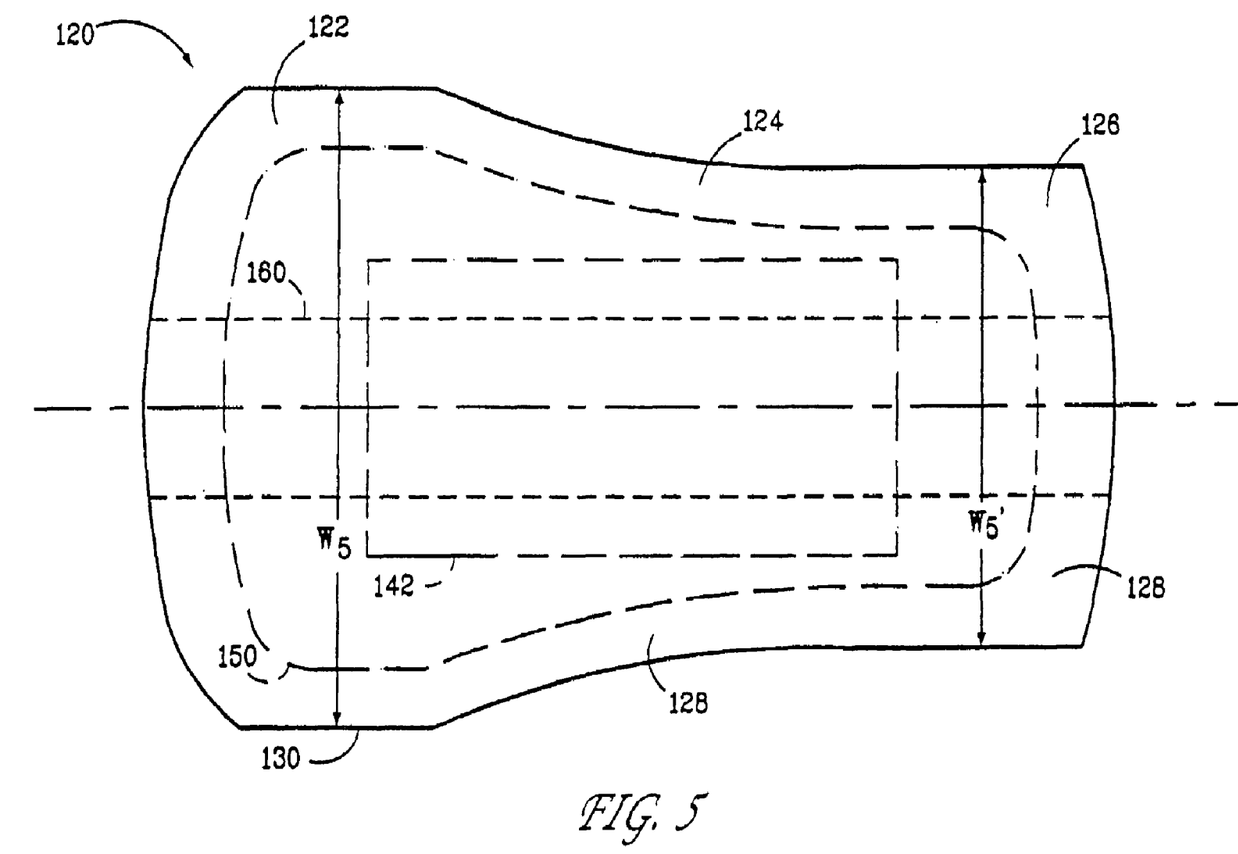
FIG. 5 is a top view of an absorbent insert according to a second embodiment of the present invention.

FIG. 5 illustrates an alternative embodiment of an insert 120 that is useful with the absorbent system of the present invention. The insert 120 is designed for use specifically by males and is dimensioned and configured to better fit to the male anatomy. The insert 120 is dimensioned and configured to be asymmetrical in that one end portion 122 has a wider dimension $W_5$ than the second end portion 126 which has a dimension $W_5'$. In a typical male adult incontinence insert, by way of example only, $W_5$ is about 12 cm to about 16 cm, whereas $W_5'$ is about 8 cm to about 12 cm. The central portion 124 is generally tapered between the first end portion 122 and the second end portion 126.

The insert 120 includes a first cover layer 130 which defines an body-facing outer surface, a second cover layer (not shown) which defines a garment-facing outer surface, a first absorbent layer 142 nearest the body-facing outer surface, a second absorbent layer 150 adjacent the first absorbent layer 142, and a delay layer 160 between the second absorbent layer 150 and the second cover layer. The second absorbent layer 150 is generally smaller and proportional to the dimensions of the first cover layer 130, thereby leaving a border area 128 in which the first cover layer 130 may be attached to the second cover layer. The first absorbent layer 142 and the delay layer 160 are both shown as being symmetrical, however, in alternate embodiments, the first absorbent layer 142 and/or the delay layer 160 may be asymmetrical. Furthermore, as in other embodiments of the insert, the arrangement of the layers may be altered, and more or fewer absorbent layers may be present. Significantly, however, in the preferred embodiment of the insert 120, the surface area of each primary surface of the delay layer 160 is less than the surface area of each primary surface of the largest absorbent layer (here, the second absorbent layer 150).

While the invention has been described in conjunction with several specific embodiments, it is to be understood that many alternatives, modifications and variations will be apparent to those skilled in the art in light of the aforegoing description. For example, the body-facing outer surface and the garment-facing outer surface have been shown as being part of the cover layers; however, the cover layers, as well as the intake or surge layer, are optional layers which need not be included in the insert. Rather, the absorbent layer itself, particularly, the covering material 43 and the wrapping material of layer 50, may serve as the outer surfaces, or the delay layer may serve as an outer surface. Furthermore, while the delay layer has been shown as being between the second absorbent layer and the garment-facing outer surface, the delay layer may also be on the other side of the absorbent layers, nearer the body-facing outer surface or between two absorbent layers. In other embodiments, there may be more than one delay layer. In another example, while the attachment portion has been shown as an adhesive zone, other mechanisms of attachment, such as mechanical fasteners, may also be used. Alternately, the insert may simply rest in the absorbent garment by way of friction, without any attachment mechanism. Accordingly, this invention is intended to embrace all such alternatives, modifications and variations that fall within the spirit and scope of the appended claims.

The invention claimed is:

1. An absorbent insert for use with an absorbent garment configured to allow fluid to pass therethrough to said absorbent garment, the insert comprising:
   a body-facing outer surface and a garment-facing outer surface, said garment-facing outer surface being at least partially fluid permeable and having a pore size that will readily allow the passage of liquids therethrough;
   at least one absorbent layer having a first primary surface and a second primary surface; and
   at least one water insoluble continuous fluid impermeable delay layer adapted to substantially affect the flow of fluid passing through the insert, said at least one continuous fluid impermeable delay layer having a first primary surface and a second primary surface;
   wherein the surface area of each of said primary surfaces of said at least one water insoluble continuous fluid impermeable delay layer is less than the surface area of each of said primary surfaces of at least one of the said at least one absorbent layers; and
   wherein said at least one delay layer is positioned between said at least one absorbent layer and said garment-facing outer surface.

2. The absorbent insert of claim 1, wherein said at least one delay layer is adapted to substantially change the flow direction of fluid passing through the insert.

3. The absorbent insert of claim 1, wherein said at least one delay layer is adapted to partially inhibit the flow of fluid through the insert.

4. The absorbent insert of claim 1, further comprising a first cover layer and a second cover layer, said body-facing outer surface comprising a surface of said first cover layer, said garment-facing outer surface comprising a surface of said second cover layer, said at least one delay layer positioned between said first cover layer and said second cover layer.

5. The absorbent insert of claim 1, wherein said at least one absorbent layer comprises a first absorbent layer and a second absorbent layer, each primary surface of said first absorbent layer having a surface area less than the surface area of each primary surface of said second absorbent layer.

6. The absorbent insert of claim 5, wherein said second absorbent layer is positioned between said at least one delay layer and said first absorbent layer.

7. The absorbent insert of claim 1, further comprising an attachment portion adapted to removably attach said insert to said absorbent garment.

8. The absorbent insert of claim 7, wherein said attachment portion comprises an adhesive zone adapted to removably attach the insert to the absorbent garment.

9. An absorbent insert for use with an absorbent garment, the insert comprising:
   a body-facing cover layer and a garment-facing cover layer, said garment-facing cover layer being at least partially fluid permeable and having a pore size that will readily allow the passage of liquids therethrough;
   at least one absorbent layer having a first primary surface and a second primary surface, said at least one absorbent layer positioned between said body-facing cover layer and said garment-facing cover layer; and
   at least one water insoluble continuous fluid impermeable delay layer having a first primary surface and a second primary surface, said at least one continuous fluid impermeable delay layer adapted to substantially affect the flow of fluid through the insert, said continuous fluid impermeable delay layer positioned between said body-facing cover layer and said garment-facing cover layer;
   wherein the surface area of each of said primary surfaces of said at least one continuous fluid impermeable delay layer is less than the surface area of each of said primary surfaces of at least one of the said at least one absorbent layer; and
   wherein said absorbent insert is configured to allow fluid to pass therethrough to said absorbent garment.

10. The absorbent insert of claim 9, wherein said at least one delay layer is adapted to substantially change the flow direction of fluid passing through the insert.

11. The absorbent insert of claim 9, wherein said at least one delay layer is adapted to partially inhibit the flow of fluid through the insert.

12. The absorbent insert of claim 9, further comprising an intake layer between said at body-facing cover layer and said at least one absorbent layer.

13. The absorbent insert of claim 9, wherein said garment-facing cover layer further comprises an attachment portion adapted to removably attach the insert to an absorbent garment.

14. An absorbent system comprising:
   an absorbent garment adapted to be worn by a user, said absorbent garment having a body-facing surface and an outward-facing surface; and
   an absorbent insert for use with the absorbent garment, said insert being configured to allow the passage of fluid therethrough to said absorbent garment and including:
   a body-facing outer surface and a garment-facing outer surface, said garment-facing outer surface being at least partially fluid permeable and having a pore size that will readily allow the passage of liquids therethrough;

at least one absorbent layer having a first primary surface and a second primary surface; and at least one water insoluble continuous fluid impermeable delay layer adapted to substantially affect the flow of fluid passing through the insert, said at least one continuous fluid impermeable delay layer having a first primary surface and a second primary surface;

wherein the surface area of each of said primary surfaces of said at least one continuous fluid impermeable delay layer is less than the surface area of each of said primary surfaces of at least one of the said at least one absorbent layer; and wherein said at least one delay layer is positioned between said at least one absorbent layer and said garment-facing outer surface.

15. The absorbent system of claim 14, wherein the absorbent insert further comprises an attachment portion adapted to removably attach said absorbent insert to said absorbent garment.

* * * * *